United States Patent [19]

Rocklage et al.

[11] Patent Number: 5,223,243
[45] Date of Patent: Jun. 29, 1993

[54] DIPYRIDOXYL PHOSPHATE CHELATING COMPOUND INTERMEDIATES USEFUL AS NMRI CONTRAST AGENTS

[75] Inventors: Scott M. Rocklage, Saratoga; Steven C. Quay, Los Altos Hills, both of Calif.

[73] Assignee: Salutar, Inc., Sunnyvale, Calif.

[21] Appl. No.: 570,115

[22] Filed: Aug. 20, 1990

Related U.S. Application Data

[62] Division of Ser. No. 370,430, Jun. 23, 1989, Pat. No. 4,992,554, which is a division of Ser. No. 47,614, May 8, 1987, Pat. No. 4,933,456.

[51] Int. Cl.$^5$ .................. A61K 49/04; C07F 9/58; C07F 1/02; C07F 13/00
[52] U.S. Cl. ............................ 424/9; 546/5; 546/6; 546/22; 546/24; 546/261
[58] Field of Search ............... 546/24, 22, 5, 6, 261; 424/9

[56] References Cited

U.S. PATENT DOCUMENTS

| | | | |
|---|---|---|---|
| 4,992,555 | 2/1991 | Rocklage et al. | 546/24 |
| 5,091,169 | 2/1992 | Rocklage et al. | 424/9 |
| 5,130,431 | 7/1992 | Rocklage et al. | 546/22 |
| 5,130,437 | 7/1992 | Rocklage et al. | 546/22 |

OTHER PUBLICATIONS

Bowers-Komro and McCormick, "Single- and Double-Headed Analogs of Pyridoxamine 5'-Phosphate as Probes for Pyridoxamine 5'-Phosphate Utilizing Enzymes", Bioorganic Chemistry 15, (1987), pp. 224–236.

Primary Examiner—Alan L. Rotman

[57] ABSTRACT

N,N'-bis-(pyridoxal-5-phosphate)-alkylenediamine-N,N'-diacetic acids, N,N'-bis-(pyridoxal-5-phosphate)-1,2-cycloalkylenediamine-N,N'diacetic acids, and N,N'-bis-(pyridoxal-5-phosphate)-1,2-arylenediamine-N,N'diacetic acids, the corresponding monophosphate compounds and monoacetic acid compounds, and their salts and esters form stable, highly soluble chelates with paramagnetic metal ions, and are highly effective NMRI contrast agents. Preferred contrast agents are paramagnetic ion chelates of N,N'-bis-(pyridoxal-5-phosphate)ethylenediamine-N,N'-diacetic acid, N,N'-bis-(pyridoxal-5-phosphate)trans-1,2-cyclohexylenediamine-N,N'-diacetic acid, N,N'-bis-(pyridoxal-5-phosphate)trans-1,2-arylenediamine-N,N'-diacetic acid, and the soluble calcium salts thereof.

Novel intermediates for forming these compounds are N,N'-bis(pyridoxal-5-phosphate)alkylenediimines, N,N'-bis(pyridoxal-5-phosphate)alkylenediamines, N,N'-bis(pyridoxal-5-phosphate)-1,2-cycloalkylenediimines, N,N'-bis(pyridoxal-5-phosphate)-1,2-cycloalkylenediamines, N,N'-bis(pyridoxal-5-phosphate)-1,2-arylenediamines, and the corresponding monophosphate compounds.

2 Claims, 1 Drawing Sheet

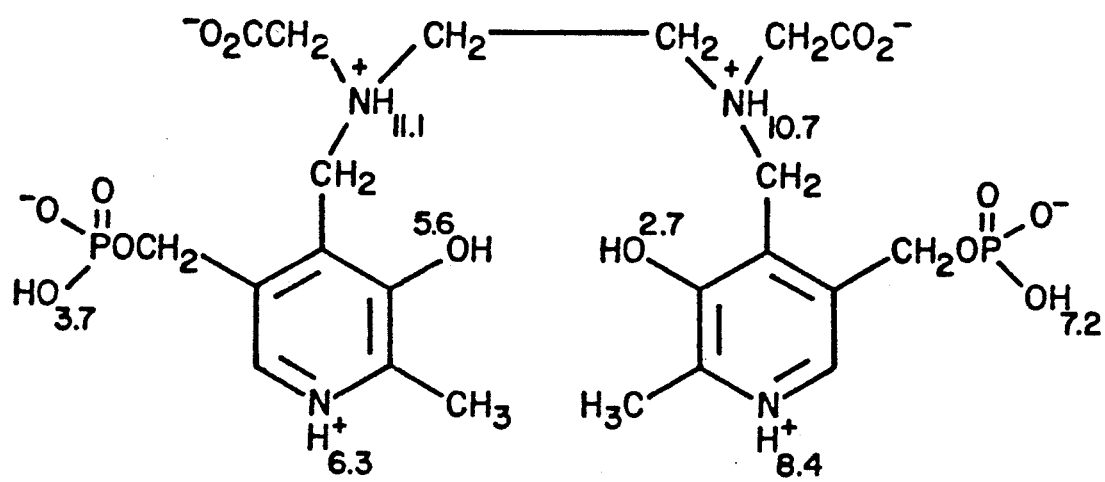
FIG._1.
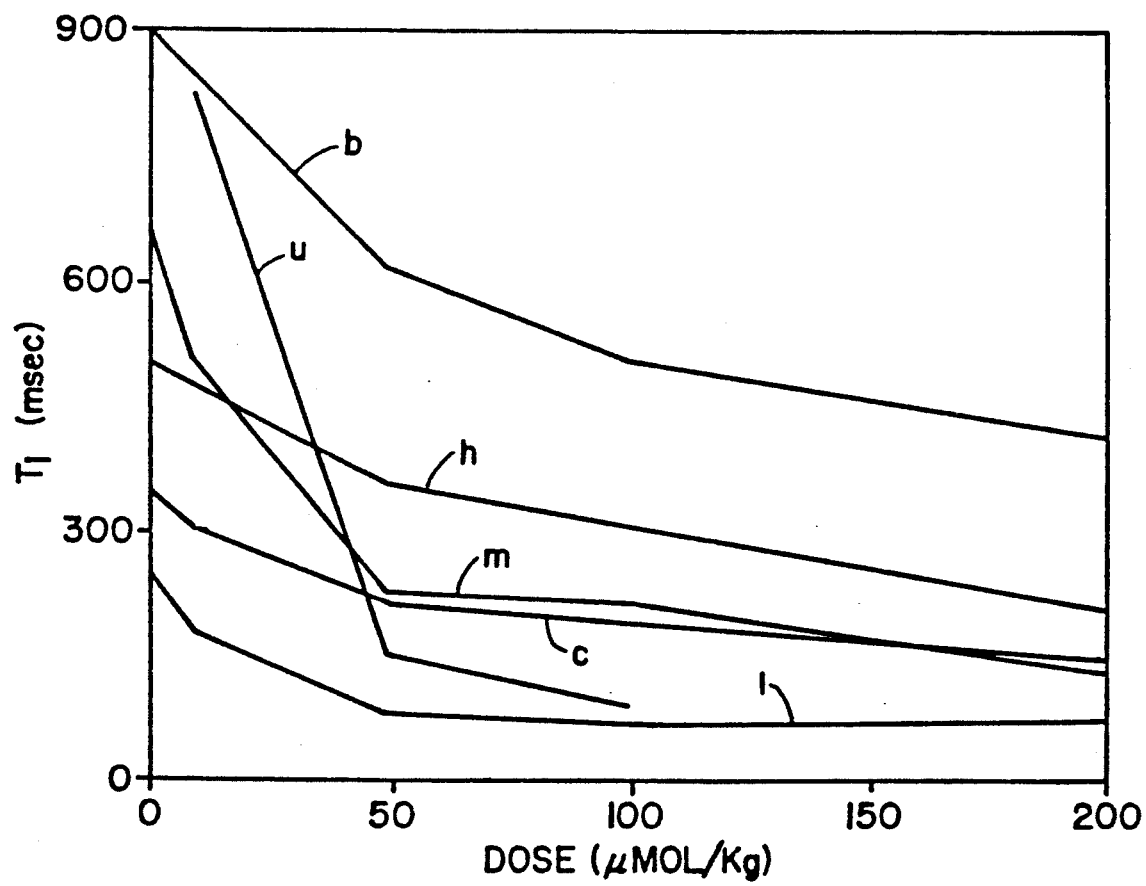
FIG._2.

DIPYRIDOXYL PHOSPHATE CHELATING COMPOUND INTERMEDIATES USEFUL AS NMRI CONTRAST AGENTS

This application is a division of copending U.S. patent application Ser. No. 07/370,430, filed Jun. 23, 1989, now U.S. Pat. No. 4,992,554, which is a division of Ser. No. 07/047,614, filed May 8, 1987, now U.S. Pat. No. 4,933,456.

FIELD OF THE INVENTION

This invention relates to novel compounds which form highly stable chelates with metal ions and which are useful as metal ion carriers for in vivo medical applications. In particular, this invention is directed to novel dipyridoxyl compounds which form highly stable chelates with polyvalent metal ions, the preparation of the compounds and chelates thereof with polyvalent ions and particularly paramagnetic ions, and the use of the paramagnetic chelates as contrast agents in nuclear magnetic resonance imagery (NMRI).

BACKGROUND OF THE INVENTION

Traditionally, chelates have been used to administer poorly soluble salts in medicine and as antidotes for detoxification in cases of heavy metal or heavy metal isotope poisoning. Chelates have also been used to deliver radioisotopes to areas of the body for imaging and radiation therapy. Most recently, chelates with paramagnetic contrast agents have been reported for use with NMRI.

Paramagnetic metal ions are frequently toxic in the concentrations required for use in NMRI, and introducing them into the body in the form of chelates renders them more physiologically acceptable. This requires that a chelate be able to hold the metal ion tightly in the chelate structure, that is, the formation constant for the chelate must be very large at physiological pH. The paramagnetic metal chelate must also be sufficiently soluble to permit administration of quantities required for imaging in reasonable volumes. Usual routes of administration are orally, intravenously and by enema.

The chelating agent must form a stable chelate with those paramagnetic metals which present a hazard to the body if released during use. Paramagnetic metals which are naturally present in the body are preferred. The chelate forming agent (ligand) must be capable of forming a chelate with a selected paramagnetic material without altering the metal's oxidation state or otherwise reducing its chemical stability.

Since the role of the paramagnetic metal in increasing contrast in NMRI imaging involves reducing the spin-lattice spin relaxation time $T_1$ and the spin-spin relaxation time $T_2$, the chelate structure must hold the metal ion tightly while permitting contact of the metal ion with protons in water molecules.

This invention provides a novel, superior chelating agent and metal complexes therewith which meet the above objectives.

DESCRIPTION OF THE PRIOR ART

A summary of the history and state of the art of contrast agents for NMRI is presented by Valk, J. et al, BASIC PRINCIPLES OF NUCLEAR MAGNETIC RESONANCE IMAGING. New York: Elsevier, pp 109–114 (1985). The Valk et al publication also describes the imaging equipment and methods for NMRI, and the entire contents of the Valk et al publication are hereby incorporated by reference in their entirety. Chelates with ethylenediaminetetraacetic acid (EDTA) and diethylaminetriaminepentaacetic acid (DTPA) are described. Toxicity problems were reduced by seeking less toxic metal ions such as iron and gadolinium in a complex of gadolinium-DTPA chelate-meglumine. Gadolinium, however, is not naturally present in the body and long term toxicity studies have not been completed. Paramagnetic materials listed in this publication include molecules with unpaired electrons: nitric oxide (NO); nitrogen dioxide ($NO_2$); and molecular oxygen ($O_2$). Also included are ions with unpaired electrons, that is ions from the "transition series". Listed ions include $Mn^{2+}$, $Mn^{3+}$, $Fe^{2+}$, $Fe^{3+}$, $Ni^{2+}$, $Cr^{2+}$, $Cu^{2+}$, the lanthanide series including gadolinium and europium, and nitroxide stable free radicals (NSFR) such as pyrrolidine NSFR and piperidine NSFR. Toxicity problems are indicated to present a major problem with many paramagnetic materials.

Use of alkylenediamine chelates with a variety of paramagnetic ions are described in U.S. Pat. No. 4,647,447. Ferrioxamine-paramagnetic contrast agents are described in U.S. Pat. No. 4,637,929. Manganese(II) is listed as a suitable paramagnetic metal ion for use with polysaccharide derivatives of a variety of chelating compounds including EDTA, DTPA and aminoethyl diphosphonate in PCT application publication no. WO85/05554 (Application No. PCT/GB85/00234). Stable radioactive diagnostics agents containing $^{99m}Tc$ chelated with N-pyridoxal-alpha-aminoacids or a pyridoxal salt are disclosed in U.S. Pat. Nos. 4,313,928, 4,440,739, and 4,489,053.

Taliaferro, C. et al in "New multidentate ligands. 22. N,N'-dipyridoxyethylenediamine-N,N'-diacetic acid: a new chelating ligand for trivalent metal ions", Inorg. Chem. 23:1188–1192 (1984) describe development of N,N'-dipyridoxyethylenediamine-N,N'-diacetic acid (PLED) as a chelating compound for trivalent metal ions. Other chelating compounds described are the Fe(III) chelates of N,N'-ethylenebis-2-(o-hydroxyphenyl)glycine (EHPG) and N,N'-bis(1-hydroxybenzyl)ethylenediamine-N,N'-diacetic acid (HBED). Properties of chelates of PLED, HBED, EHPG and EDTA with ions of copper, nickel, cobalt, zinc, iron, indium and gallium are compared. Investigation of the structure of PLED is reported by Taliaferro, C. et al, Inorg.-Chem. 24:2408–2413 (1985). Green, M. et al, Int.J.Nucl.Med.Biol. 12(5):381–386 (1985) report their evaluation of PLED as a chelating ligand for the preparation of gallium and indium radiopharmaceuticals, and summarize properties of PLED chelates with Ga(III), In(III), and Fe(III).

Because the compounds of this invention have an aromatic hydroxy group, their value as chelating agents for manganese(II) ions would not be expected; such aromatic hydroxy groups would be expected to react with the manganese(II) ion as an oxidant in the usual way, oxidizing the manganese(II) ion to a higher valence. Frost, et al, J.Am.Chem.Soc. 80:530 (1958) report the formation of Mn(II) chelates of EHPG at low pH, but found that attempts to prepare stable manganese(II) complexes with EHPG at higher pH's (above pH 5) was futile as the manganese(II) ion was irreversibly oxidized. This oxidation occurred even under inert atmospheres, and the writers concluded that the oxidation occurred at the expense of the ligand or solvent. Anderegg, G. et al, Helv.Chim.Acta. 47:1067 (1964) found the high stability of the Fe(III) chelate of EHPG was due to the high affinity of the Fe(III) ion for the two phenolate groups present in the ionized ligand. L'Eplathenier, F. et al, (J.Am.Chem.Soc. 89:837 (1967) describes studies of HBED involving acid titrations of HBED in the presence of a variety of metal ions, including manganese(II). No manganese chelate was isolated, and the manganese products were not characterized. Based on subsequent work by Patch et al, Inorg.Chem. 21(8):2972-2977 (1982), it is clear that the manganese(II) ion was oxidized by the phenolic ligand during the titrations of L'Eplathenier et al. Patch et al prepared a Mn(III) complex by reacting Mn(II) salts with EHPG, and concluded the reaction involved the oxidation of the ligand in an irreversible reaction. The ability to maintain Mn(III) in the +3 oxidation state was said to be a unique characteristic of the EHPG molecule. U.S. Pat. No. 3,632,637 describes phenolic chelating agents such as N,N'-di(o-hydroxylbenzyl)-ethylenediamine-N,N'-diacetic acid and their use in chelating trivalent and tetravalent metals. These agents are usually stable in the presence of aromatic hydroxy groups. No use of a compound with an aromatic hydroxy group as a chelating agent for manganese(II) ions is disclosed in these references, confirming the general knowledge about the oxidizing properties of the aromatic hydroxy group on manganese compounds, in particular manganese(II) ions.

SUMMARY OF THE INVENTION

The novel chelate forming compounds of this invention are shown in Formula I.

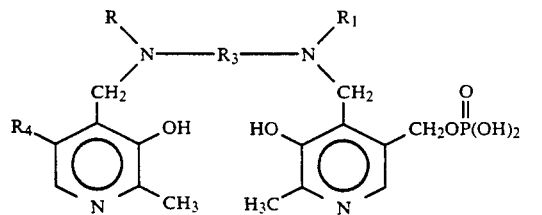 (I)

wherein
R is hydrogen or

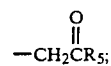

$R_1$ is hydrogen or

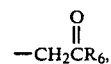

and one of R and $R_1$ is other than hydrogen;
$R_3$ is alkylene having from 1 to 8 carbons, 1,2-cycloalkylene having from 5 to 8 carbons, or 1,2-arylene having from 6 to 10 carbons, and
$R_4$ is hydrogen, alkyl having from 1 to 6 carbons or

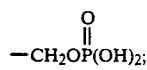

$R_5$ and $R_6$ are each, individually, hydroxy, alkoxy having from 1 to 18 carbons, hydroxy-substituted alkoxy having from 1 to 18 carbons, amino or alkylamido having from 1 to 18 carbons.

The phosphate group mono and diesters with mono and polyhydric alkanols having from 1 to 18 carbons, or alkylamino alcohols, each having from 1 to 18 carbons, and the salts of the above compounds are included within the scope of this invention.

Also included in this invention are the chelates of the compounds of Formula I and salts and esters thereof with metal ions, preferably paramagnetic metal ions having atomic numbers of from 21-29, 42, 44 and 58-70, and optimally manganese(II), and their use as imaging agents.

The novel intermediate compounds from which the compounds of Formula I are prepared are also included within the compounds of this invention.

BRIEF DESCRIPTION OF THE DRAWING

FIG. 1 shows a structural formula of a species of N,N'-bis(pyridoxal-5-phosphate)ethylenediamine-N,N'-diacetic acid, showing the dissociation constants, pK's, as assigned to the protonation sites described in Example 11.

FIG. 2 is a graph showing the relationship between dosage and relaxivity using the Mn(DPDP) compound of this invention based on the data shown in Example 9.

DETAILED DESCRIPTION OF THE INVENTION

The novel chelate forming compounds of this invention are shown in Formula I. The pharmaceutically acceptable water-soluble compatible salts of the compounds of Formula I and phosphate group esters of the compounds of Formula I with polyhydric alcohols, aliphatic alcohols, or alkylamino alcohols, each having from 1 to 18 carbons, and the chelates thereof are also included within the compounds of this invention.

In Formula I, $R_5$ and $R_6$ are preferably each individually hydroxy, alkoxy having from 1 to 8 carbons, ethylene glycol, glycerol, amino or alkylamido having from 1 to 8 carbons. Optimally, $R_5$ and $R_6$ are hydroxy and the salts thereof.

The term "alkyl" and "alkylene", as used herein, include both straight and branch-chained, saturated and unsaturated hydrocarbons. The term "1,2-cycloalkylene" includes both cis and trans cycloalkyl groups and alkyl substituted cycloalkylene groups bonded at the 1,2-positions to respective nitrogen atoms and alkyl substituted derivatives thereof having from 5 to 8 carbons. The term "1,2-arylene" includes phenyl and naphthyl groups bonded at the 1,2-positions to respective nitrogen atoms and alkyl substituted derivatives thereof, having from 6 to 10 carbons.

The compound, N,N'-bis-(pyridoxal-5-phosphate)ethylenediamine-N,N'-diacetic acid or N,N'-bis(3-hydroxy-2-methyl-5-phosphonomethyl-4-pyridylmethyl)ethylenediamine-N,N'-diacetic acid, is referred to hereinafter as DPDP, and the Manganese(II) chelate is referred to hereinafter as Mn(DPDP).

The dicarbonyl compound of Formula I, when $R_5$ and $R_6$ are hydroxy and $R_3$ is ethylene, is DPDP. DPDP has the dissociation constants for the protonation sites shown in FIG. 1. As described in Example 11, at pH of 3 and above, the ligand is anionic and possesses deprotonated metal binding sites, both important criteria for metal chelating agents.

CHELATES

The chelates of this invention are chelates of the compounds of Formula I with metal ions. The chelates can be represented by Formulas II, III or IV.

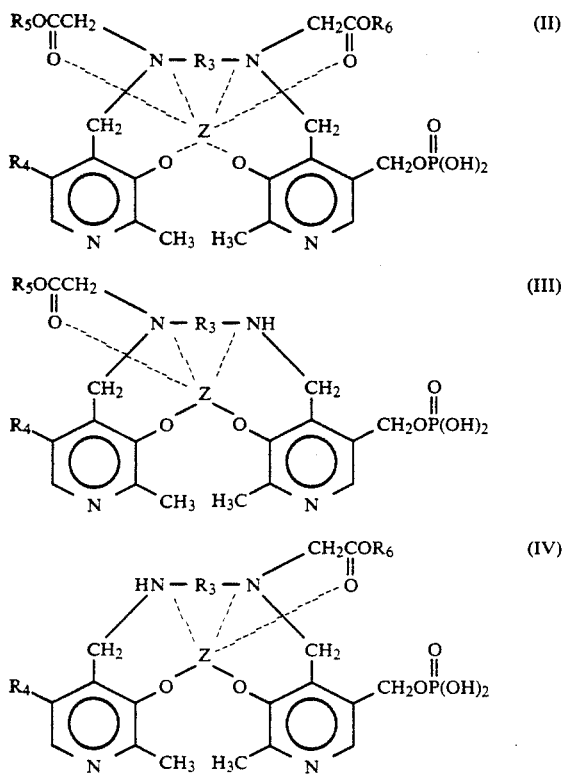

In Formulas II, III and IV, Z represents a metal ion and $R_3$, $R_4$, $R_5$ and $R_6$ are the same as described with respect to the compounds of Formula I. The dotted lines in the figure represent the dative bonding between the oxygen and nitrogen atoms and the metal ion. One of the acetyl groups in Formula II is below the plane of the aromatic pyridine rings and the other acetyl group is above the plane of the aromatic pyridine rings, so the metal ion is tightly held within the interior of the chelate salt complex with the dicarboxy embodiments of this invention. Also included in the chelates of this invention are the pharmaceutically acceptable water-soluble compatible salts, and carboxylic and phosphate group esters with hydroxy-substituted alkanols, alkanols, or alkylamino alcohols, each having from 1 to 18 carbons, of the compounds of Formulas II, III, and IV.

For use as a medium for NMRI analysis, the central ion of the complex chelate salt must be paramagnetic, and preferably is a divalent or trivalent ion of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium(III), ytterbium(III). Gadolinium(III), terbium(III), dysprosium(III), holmium(III) and erbium(III) are sometimes preferred because of their strong magnetic moments and chemical stability, but because they are not normally present in the body, their long term biological effects are unknown.

With the novel chelate forming compounds of Formula I, chelates of manganese(II) are preferred. Relatively few manganese(II) chelate compounds are known, and only a fraction of these have been characterized i.e., by single crystal X-ray diffraction. Most of the structurally characterized Mn(II) complexes have various mono and bidentate ligands coordinating to the metal center. The Mn(II) complexes of Formulas II, II and III, and the Mn(II) complexes with PLED and the corresponding 1,2-cycloalkylene and 1,2-arylene compounds described in our co-pending, concurrently filed application, U.S. Ser. No. 07/047,594, filed May 8, 1987, titled MANGANESE(II) CHELATE CONTRAST AGENTS AND METHODS are the first Mn(II) complexes with a high affinity hexadentate ligand. This configuration provides a more stable and effective form for introducing manganese(II) into the body as a NMRI contrast medium.

The manganese(II) complex of Formula II ($R_5$ and $R_6$=hydroxy, $R_3$=ethylene), Mn(DPDP), was studied potentiometrically from pH 11.1 to 2.0. The data obtained was analyzed using a model consisting of three one proton steps and one two proton step. Refinement yielded equilibrium constants with calculated e.s.d.'s (log K) of less than 0.02. The log $K_f$ (formation constant) for Mn(DPDP) was calculated to be 14.8 and is identical to that of the manganese chelate of N,N'-bis(2-hydroxybenzyl)ethylenediamine-N,N'-diacetic acid (HBED) reported by L'Eplathenier, F. et al (supra). The titration data indicates that Mn(DPDP) begins to demetallate as the pH drops below 4.5. At physiological pH, however, the Mn(II) ion is quantitatively bound to the chelating agent, stabilized at the +2 valence.

The chelate forming compounds of this invention are also suitable for forming chelate salts of other metals intended for X-ray diagnosis. In general, these are the elements of an atomic number which is sufficiently high to efficiently absorb X-rays. Diagnostic media containing a physiologically well tolerated chelate salt with central ions of elements with atomic numbers of 57 to 83 are suitable for this purpose. Included in this group are lanthanum(III), gold(III), lead(II), and bismuth(III).

All of the chelates according to this invention useful for NMRI and X-ray analysis are also suitable for use in ultrasonic diagnosis.

The elements of the above-listed atomic numbers which form the central ion or ions of the physiologically well tolerated chelate salt, must not be radioactive for the intended use of the diagnostic medium for X-ray diagnosis and NMRI. Radioactive metal ion chelates of the compounds of Formula I are described in our U.S. Pat. No. 4,842,845, issued Jun. 27, 1989 DIPYRIDOXYL PHOSPHATE RADIOACTIVE METAL CHELATES.

For purposes of clarity, the chelates of this invention will be described hereinafter in terms of paramagnetic ions suitable for use in NMRI analysis. However, this is for purposes of clarity of explanation and not by way of limitation, and chelates of all of the above metal ions are included within the scope of this invention.

If not all of the active hydrogen atoms of the chelates are substituted by the central paramagnetic ion, the solubility of the chelate is increased if the remaining hydrogen atoms are substituted with physiologically biocompatible cations of inorganic and/or organic bases or amino acids. For example, the lithium ion, the potassium ion, the sodium ion and especially the calcium ion are suitable inorganic cations. Suitable cations of organic bases include, for example, ethanolamine, diethanolamine, morpholine, glucamine, N,N-dimethylglucamine, and N-methylglucamine. Lysine, arginine or orithine are suitable as cations of amino acids, as generally are those of other basic naturally occurring acids.

The preferred calcium salts have calcium ion to chelating molecule mole ratios of from 0.05 to 1.0, the optimum mole ratios being with the range of from 0.1 to 0.5. At mole ratios of calcium ion to chelate molecule above 1.0, the chelate tends to become insoluble. The soluble calcium salts are most physiologically acceptable since they do not significantly disturb the concentration of free calcium ions in the patient's system.

The chelates according to this invention are formed form the chelate forming compounds of Formula I by conventional procedures known in the art. In general, these processes involve dissolving or suspending the metal oxide or metal salt (for example, nitrate, chloride or sulfate) of an element with an atomic number of 21 to 29, 42, 44 or 57 to 83 (for example, oxides or salts of $Mn^{+2}$, $Cr^{+3}$, $Fe^{+2}$, $Fe^{+3}$, $Co^{+3}$, $Ni^{+2}$, $Cu^{+2}$, $Pr^{+3}$, $Nd^{+3}$, $Sm^{+3}$, $Yb^{+3}$, $Gd^{+3}$, $Tb^{+3}$, $Dy^{+3}$, $Ho^{+3}$, or $Er^{+3}$) in water or a lower alcohol such as methanol, ethanol or isopropanol. To this solution or suspension is added an equimolar amount of the chelating acid in water or a lower alcohol, and the mixture is stirred, if necessary, with heating moderately or to the boiling point, until the reaction is completed. If the chelate salt formed is insoluble in the solvent used, the reaction product is isolated by filtering. If it is soluble, the reaction product is isolated by evaporating the solvent to dryness, for example, by spray drying or lyophilizing.

If acid groups such as the phosphoric acid groups are still present in the resulting chelate, it is advantageous to convert the acidic chelate salt into a neutral chelate salt by reaction with inorganic and/or organic bases or amino acids, which form physiologically biocompatible cations, and to isolate them. This is often unavoidable since the dissociation of the chelate salt is moved toward neutrality to such an extent by a shift in the pH value during the preparation that only in this way is the isolation of homogeneous products or at least their purification made possible. Production is advantageously performed with organic bases or basic amino acids. It can also be advantageous, however, to perform the neutralization by means of inorganic bases (hydroxides, carbonates or bicarbonates) of sodium, potassium or lithium.

To produce the neutral salts, enough of the desired base can be added to the acid chelate salts in an aqueous solution or suspension that the point of neutrality is reached. The resulting solution can then ben concentrated to dryness in vacuo. It is often advantageous to precipitate the neutral salts by adding a solvent miscible with water, for example, lower alcohols (methyl, ethyl, isopropyl alcohols, etc.), lower ketones (acetone, etc.), polar ethers (tetrahydrofuran, 1,2-dimethoxyethane, etc.) and thus obtain crystals that isolate easily and purify well. It has been found particularly advantageous to add the desired bases to the reaction mixture even during chelating and thus eliminate a process stage. Other conventional purification procedures such as column chromatography can be used.

Since the chelate salts of Formulas II, III and IV contain a plurality of acid groups, it is possible to produce neutral mixed salts which contain both inorganic and organic physiologically biocompatible cations as counterions. This can be done, for example, by reacting the complexing acids in an aqueous suspension or solution with the oxide or salt of the element supplying the central ion or less than the full amount of an organic base necessary for neutralization, e.g., half, isolating the chelate salt that is formed, purifying it, if desired, and then adding it to the amount of inorganic base necessary for complete neutralization. The sequence of adding the bases can be reversed.

The carboxylic and phosphoric acid groups of the chelating agents can also be neutralized by esterification to prepare carboxylate and phosphate esters. Such esters can be prepared by conventional procedures known in the art, for example, from the corresponding alcohols. Suitable esters include, for example, esters of straight or branch-chained alkanol groups having from 1 to 18 carbons, mono and polyhydric alkyl amino alcohols having from 1 to 18 carbons and preferably from 1 to 6 carbons such as serinol or diethanolamine, and polyhydric alcohols having from 1 to 18 and preferably from 1 to 6 carbons such as ethylene glycol or glycerol.

The diagnostic media for administration is formed using physiologically acceptable media in a manner fully within the skill of the art. For example, the chelate salts, optionally with the addition of pharmaceutically acceptable excipients, are suspended or dissolved in an aqueous medium, and then the solution or suspension is sterilized. Suitable additives include, for example, physiologically biocompatible buffers (as, for example, tromethamine hydrochloride), slight additions of other chelating agents (as for example, diethylenetriaminepentacetic acid) or, if optimally, calcium salts (for example, calcium chloride, calcium ascorbate, calcium gluconate or calcium lactate).

Alternatively, the diagnostic media according to this invention can be produced without isolating the chelate salts. In this case, special care must be taken to perform the chelating so that the salts and salt solutions according to the invention are essentially free of unchelated, potentially toxic metal ions. This can be assured, for example, using color indicators such as xylenol orange to control titrations during the production process. A purification of the isolated salt chelate can also be employed as a final safety measure.

If suspensions of the chelate salts in water or physiological salt solutions are desired for oral administration, a small amount of soluble chelate salt can be mixed with one or more of the inactive ingredients traditionally present in oral solutions, surfactants and/or aromatics for flavoring and the like.

The most preferred mode for administering paramagnetic metal chelates as contrast agents for NMRI analysis is by intravenous administration. Intraveneous solutions must be sterile, free from physiologically unacceptable agents, and should be isotonic or iso-osmotic to minimize irritation or other adverse effects upon administration. Suitable vehicles are aqueous vehicles customarily used for administering parenteral solutions such as Sodium Chloride Injection, Ringer's Injection, Dextrose Injection, Dextrose and Sodium Chloride Injection, Lactated Ringer's Injection, and other solutions such as are described in REMINGTON'S PHARMACEUTICAL SCIENCES. 15th Ed., Easton: Mack Publishing Co. pp 1405-1412 and 1461-1487 (1975) and THE NATIONAL FORMULARY XIV. 14th Ed. Washington: American Pharmaceutical Association (1975), the contents of which are hereby incorporated by reference. The solutions can contain preservatives, antimicrobial agents, buffers and antioxidants conventionally used in parenteral solutions, selecting excipients and other additives which are compatible with the chelates and which will not interfere with the manufacture, storage or use of the products.

The diagnostic media according to this invention can contain from 0.001 to 5.0 moles per liter and preferably from 0.1 to 0.5 moles per liter of the chelate salt.

The chelates of this invention are administered to patients for imaging in amounts which are sufficient to yield the desired contrast. Generally, dosages of from 0.001 to 5.0 mmoles of contrast agent per kilogram of patient body weight are effective to achieve reduction of relaxivity rates. The preferred dosages for most NMRI applications are from 0.02 to 0.5 mmoles of contrast agent per kilogram of patient body weight.

Methods for applying the contrast agents to improve NMRI images, equipment and operating procedures are described by Valk, J. et al, supra. The contrast agents can be used orally and intravenously.

In a novel NMRI application, the contrast agents can be introduced into the cervix, uterus and fallopian tubes. NMR imaging can then be performed to detect causes of infertility such as obstructions or imperfections in the internal surface of the fallopian tubes which might interfere with the movement of the fertilized ovum.

CHELATE FORMING COMPOUNDS

The compounds of Formula I can be formed by reacting the corresponding pyridoxal 5-phosphate (3-hydroxy-2-methyl-5-phosphonomethyl-4-pyridinecarboxyaldehyde) represented by Formula V with a diamine represented by Formula VI.

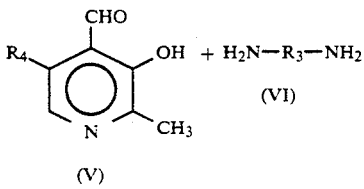

In the compounds of Formula V and VI, $R_3$ and $R_4$ are as defined with respect to Formula I. Pyridoxyl 5-phosphate, pyridoxal, and the other compounds of Formula V, and the alkylenediamine, cycloalkylenediamine and arylene reactants of Formula VI are well known compounds readily available from commercial sources, and they can be readily synthesized by well known procedures fully within the skill of the art.

The reaction of the amino groups of the compounds of Formula VI with the aldehyde group of the compounds of Formula V can be carried out in an alcohol such as methanol at a temperature within the range of from 0° C. to 60° C. The diimines formed are represented by Formula VII.

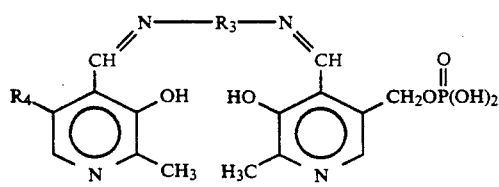

In the compounds of Formula VII, $R_3$ and $R_4$ are the same as described with respect to the compounds of Formula I. For the manufacture of compounds wherein $R_4$ is a phosphonomethyl group, i.e., the 5-(N-(3-hydroxy-2-methyl-5-phosponomethyl-4-pyridyl)methylideneaminoalkyleneiminomethyl)-2-hydroxy-3-methyl-5-pyridylmethylphosphoric acids, 5-(N-(3-hydroxy-2-methyl-5-phosponomethyl-4-pyridyl)methylideneamino-1,2-cycloalkyleneiminomethyl)-2-hydroxy-3-methyl-5-pyridylmethyl phosphoric acids, and 5-(N-(3-hydroxy-2-methyl-5-phosponomethyl-4-pyridyl)methylideneamino-1,2-aryleneiminomethyl)-2-hydrox y-3-methyl-5-pyridylmethyl phosphoric acids of Formula VII, a diamine of Formula VI is reacted with two molar equivalents of an aldehyde of Formula V having the 5-phosphonomethyl group such as pyridoxyl 5-phosphate. For preparation of compounds of Formula VII wherein $R_4$ is other than a phosphonomethyl group, the diamine of Formula VI is first reacted with only one molar equivalent of an aldehyde of Formula V having the 5-phosphonomethyl group, and the mono-phosphonomethyl reaction product is reacted with one molar equivalent of a compound of formula V having the desired $R_4$ group, such as a 5-hydroxymethyl group, i.e, pyridoxal. The reverse order of reaction can also be used. The reaction products of Formula VII are insoluble in the alcohol and can be isolated by filtration.

The compounds of formula VII are then hydrogenated by conventional procedures using a palladium or platinum catalyst to yield the diamines of Formula VIII.

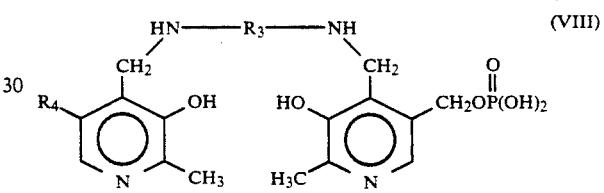

In the compounds of Formula VIII, $R_3$ and $R_4$ are the same as described with respect to the compounds of Formula IV. The 5-(N-(3-hydroxy-2-methyl-5-phosponomethyl-4-pyridyl)-methylaminoalkyleneaminomethyl)-2-hydr oxy-3-methyl-5-pyridylmethylphosphoric acids, 5-(N-(3-hydroxy-2-methyl-5-phosponomethyl-4-pyridyl)methylamino-1,2-cycloalkyleneaminomethyl)-2-hydro xy-3-methyl-5-pyridylmethyl phosphoric acids, 5-(N-(3-hydroxy-2-methyl-5-phosponomethyl-4-pyridyl)methylamino-1,2-cycloaryleneaminomethyl)-2-hydrox y-3-methyl-5-pyridylmethyl phosphoric acids, and the monophosphonomethyl compounds of Formula VIII can be left in solution or isolated as crystalline solids.

The compounds of Formula I are prepared by reacting the diamines of Formula VIII with a haloacetic acid such as bromoacetic acid, the molar ratio of the bromoacetic acid to diamine determining whether one or both of the amines are conjugated with the acetic acid groups. The N,N'-bis(3-hydroxy-2-methyl-5-phosphonomethyl-4-pyridylmethyl)alkylenediamine-N,N'-diacetic acids, N,N'-bis(3-hydroxy-2-methyl-5-phosphonomethyl-4-pyridylmethyl)-1,2-cycloalkylenediamine-N,N'-diacetic acids, N,N'-bis(3-hydroxy-2-methyl-5-phosphonomethyl-4-pyridylmethyl)-1,2-arylenediamine-N,N'-diacetic acids, N,N'-bis(3-hydroxy-2-methyl-5-phosphonomethyl-4-pyridylmethyl)alkylenediamine-N-acetic acids, N,N'-bis(3-hydroxy-2-methyl-5-phosphonomethyl-4-pyridylmethyl)-1,2-cycloalkylenediamine-N-acetic acids, and N,N'-bis(3-hydroxy-2-methyl-5-phosphonomethyl-4-pyridylmethyl)-1,2-arylenediamine-N-acetic acids of Formula I are then isolated and purified by conventional procedures such as recrystallization or anion exchange chromatography.

The carboxylic acid esters and amides can be formed by conventional procedures reacting the carboxylic acids with alkanols having from 1 to 18 carbons, hydroxy-substituted alkanols having from 1 to 18 carbons, ammonia, and alkylamines having from 1 to 18 carbons.

This invention is further illustrated by the following specific but non-limiting examples. Temperatures are given in degrees centigrade and concentrations as weight percents unless otherwise specified. Procedures which are constructively reduced to practice herein are described in the present tense, and procedures which have been carried out in the laboratory are set forth in the past tense.

EXAMPLE 1

N,N'-bis(pyridoxal-5-phosphate)ethylenediimine

A 265.2 gm (1 mole) quantity of pyridoxal-5-phosphate (Chemical Dynamics Corp., South Plainfield, NJ) was slurried in one liter of methanol, and 400 ml of 5M NaOH was added. When the solution was homogeneous, 34.2 ml of 1,2-diaminoethane (Aldrich Chem. Co.) was added rapidly with vigorous stirring. The imine product sodium N,N'-bis(pyridoxal-5-phosphate)ethylenediimine or sodium 5-(N-(3-hydroxy-2-methyl-5-phosponomethyl-4-pyridyl)methylideneaminoethyleneiminomethyl)-2-hydroxy-3-methyl-5-pyridylmethylphosphate was stirred for 1 hr, 400 ml of diethyl ether was added, and the slurry was filtered. The filtrate was washed with 600 ml of ethanol and dried at 60° C. in vacuo. A 290 gm quantity of the bis-imine with a melting point of 215° C.–220° C. (decomposition) was isolated (90% yield, based on the tetra-sodium salt). IR (KBr) pellet: 1630 cm$^{-1}$ (C=N), $^1$H NMR (D$_2$O, 400 MHz) delta 8.88 (s, —N=CH), 7.54 (s, pyr-H), 4.70 (d, CH$_2$OP, J$_{HP}$=6.3 Hz), 4.06 (s, NCH$_2$CH$_2$N), 2.21 (s, pyr-CH$_3$).

EXAMPLE 2

N,N'-bis(pyridoxal-5-phosphate)alkyldiimines

Repeating the procedure of Example 1 but replacing the 1,2-diaminoethane with 1,3-diamino-n-propane, 1,2-diamino-n-propane, 1,2-diaminoisopropane, 1,2-diamino-n-butane, 1,4-diamino-n-butane, 1,3-diamino-n-butane, 1,2-diamino-3-methylpropane yields the corresponding N,N'-bis(pyridoxal-5-phosphate)-1,3-(n-propylene)diimine, N,N'-bis(pyridoxal-5-phosphate)-1,2-(n-propylene)diimine, N,N'-bis(pyridoxal-5-phosphate)-1,2-isopropylenediimine, N,N'-bis(pyridoxal-5-phosphate)-1,2-(n-butylene)diimine, N,N'-bis(pyridoxal-5-phosphate)-1,4-(n-butylene)diimine, N,N'-bis(pyridoxal-5-phosphate)-1,3-(n-butylene)diimine, and N,N'-bis(pyridoxal-5-phosphate)-1,2-(3-methyl)propylenediimine.

EXAMPLE 3

N,N'-bis(pyridoxal-5-phosphate)ethylenediamine

The diimine from Example 1 was charged to a 5 liter 3-neck flask fitted with mechanical stirrer, fritted tube bubbler, and a 3-way stopcock. Then 1.5 liters of deionized water was added, followed by 1.5 liters of methanol. The yellow solution formed was stirred while sparging with nitrogen. Then 13 gm of 5% Pt on carbon (Aldrich Chem. Co.) was added, and the apparatus was purged with hydrogen. The reaction was allowed to proceed for 5 hr with continuous addition of hydrogen. HPLC analysis showed complete reduction to the amine. The reaction mixture was sparged with nitrogen for 15 min and then filtered through Celite. The filtrate was concentrated in vacuo at 60° C. to about 500 ml. The solution, containing N,N'-bis(pyridoxal-5-phosphate)ethylenediamine or 5-(N-(3-hydroxy-2-methyl-5-phosponomethyl-4-pyridyl)methylaminoethyleneaminomethyl)-2-hydroxy-3-methyl-5-pyridylmethylphosphoric acid salt was used directly for the next step. If desired the diamine can be isolated as off-white crystals by the addition of 200 ml of 97% formic acid and allowing the product to crystallize at room temperature overnight. The diamine is isolated by filtration and washed with 2 ×150 ml of cold deionized water. $^1$H NMR (D$_2$O, 400 MHz) delta 7.47 (s, pyr-H), 4.58 (d, CH$_2$OP, J$_{HP}$=6.3 Hz), 3.94 (s, NCH$_2$CH$_2$N), 2.88 (s, N-CH$_2$-pyr), 2.16 (s, pyr-CH$_3$).

EXAMPLE 4

N,N'-bis(pyridoxal-5-phosphate)alkyldiamines

Repeating the procedure of Example 3 but substituting the diimine products of Example 2 for the diimine product of Example 1 yields N,N'-bis(pyridoxal-5-phosphate)-1,3-(n-propylene)diamine, N,N'-bis(pyridoxal-5-phosphate)-1,2-(n-propylene)diamine, N,N'-bis(pyridoxal-5-phosphate)-1,2-isopropylenediamine, N,N'-bis(pyridoxal-5-phosphate)-1,2-(n-butylene)diamine, N,N'-bis(pyridoxal-5-phosphate)-1,4-(n-butylene)diamine, N,N'-bis(pyridoxal-5-phosphate)-1,3-(n-butylene)diamine, and N,N'-bis(pyridoxal-5-phosphate)-1,2-(3-methyl)propylenediamine.

EXAMPLE 5

DPDP Synthesis

The diamine from Example 3 was charged to a two liter 4-neck flask equipped with two addition funnels, pH electrode, thermometer and stir bar. A 100 gm (2.5 mole) quantity of NaOH was dissolved in 200 ml of deionized water, and 130 gm (0.9 mole) of bromoacetic acid (Sigma Chem. Co.) was dissolved in 180 ml of deionized water. Each solution was charged to an addition funnel. Enough NaOH solution was added to the diamine solution to bring the pH to 11. The temperature of the reaction was raised to 42° C., and bromoacetic acid and NaOH solution were added concurrently to maintain the pH at 11. The addition was stopped at 45 min, and the progress of the reaction was checked by HPLC. The addition of bromoacetic acid and NaOH was resumed, and the reaction checked at 60 and 75 min. All the bromoacetic acid had been added, and the reaction was complete by HPLC analysis. Approximately 30 ml of the 50% NaOH solution remained in the addition funnel. A 675 gm quantity of cation exchange resin (AMBERLITE IRC-50) was added, and the mixture was placed in a refrigerator for 14 hr. The pH had dropped to 6.5. The resin was removed by filtration, and the filtrate treated with 260 gm of cation exchange resin (DOWEX 50W-X8). The pH dropped to about 4. The resin was removed by filtration, and the solution was concentrated in vacuo at 60° C. to a viscous oil. The oil was dried in vacuo for 48 hr at 25° C. to yield a resinous solid containing N,N'-bis-(pyridoxal-5-phosphate)ethylenediamine-N,N'-diacetic acid or N,N'-bis(3-hydroxy-2-methyl-5-phosphonomethyl-4-pyridylmethyl)ethylenediamine-N,N'-diacetic acid (DPDP).

EXAMPLE 6

DPDP Purification

The resinous solid obtained in Example 5 was dissolved in 600 ml of 88% formic acid, 1.5 liters of methanol followed by 2.2 liters of ethanol was added, and the mixture was cooled to 0° C. for 2 hr. The solvent mixture was decanted from the resulting gum and discarded. The gum was dissolved in about 800 ml of deionized water which was then concentrated in vacuo to about 600-650 ml. Seed crystals were added, and the solution was allowed to stand at rm temp overnight. The product was isolated by filtration, washed with about 400 ml of cold deionized water, 250 ml of ethanol, and then dried in vacuo to yield 65 gm of DPDP in 85-90% purity by HPLC. The filtrate and washings were retained, concentrated in vacuo to about 350 ml, and the solution refrigerated until column chromatographic purification of the second crop.

The 65 gms of product was then dissolved in 75 ml of 88% formic acid containing 5 ml of deionized water with gentle heating to about 60° C. Cold deionized water was added to a total volume of one liter, and the solution was allowed to stand at 25° C. for 16 hr to crystallize. The product was isolated by filtration, washed with 200 ml cold deionized water, and dried in vacuo at 60° C. to yield 55 gms of DPDP in 93-95% purity by HPLC. A second recrystallization, using the same procedure yields 50 gm of DPDP in 96-98% purity by HPLC, mp174° C.-180° C. with decomposition. Analysis: (Calculated for $C_{22}H_{32}N_4O_{14}P_2$) C, 41.38; H, 5.05; N, 8.77. (Found) C, 40.70; H, 5.14; N, 8.61. $^1H$ NMR ($D_2O$, 400 MHz) delta 7.93 (s, pyr-$\underline{H}$), 4.81 (d, $CH_2OP$, $J_{HP}$=6.3 Hz), 4.07 (s, $NCH_2C\underline{H_2N}$), 3.35 (s, $C\underline{H_2}COOH$), 2.83 (s, N-$C\underline{H_2}$-pyr), 2.38 (s, pyr-$C\underline{H_3}$). $^{31}P$ NMR ($D_2O$, 161 MHz) delta −1.61 (s, $CH_2O\underline{P}$, $H_3PO_4$ reference).

EXAMPLE 7

Sodium-Calcium Salt of Mn(DPDP)

A 4.16 gm (6.25 mmole) portion of DPDP from Example 6 was dissolved in 15 ml of rigorously degassed water by the addition of 1.0 gm (25 mmoles) of NaOH. A 1.25 gm (6.25 mmole) quantity of manganese dichloride tetrahydrate was added, and the solution immediately turned yellow. After stirring for 30 min, 0.25 gm (6.25 mmole) of solid NaOH was added to bring the pH up to 6.5. Then 0.15 gm (1.0 mmole) of calcium chloride was added, and sufficient degassed water was added to bring the volume of the solution to 25 ml. The clear yellow solution was sterilized by being filtered through a 0.2 micron filter to yield the sodium-calcium salt of a manganese chelate complex of N,N'-bis-(pyridoxal-5-phosphate)ethylenediamine-N,N'-diacetic acid or N,N'-bis(3-hydroxy-2-methyl-5-phosphonomethyl-4-pyridylmethyl)ethylenediamine-N,N'-diacetic acid.

EXAMPLE 8

Relaxivities with Mn(DPDP)

The relations of protons present in water and plasma exposed to the chelate product of Example 7 was tested by NMR for relaxities, in msec, at 10 MHz, 37° C. The results are shown in Table I.

TABLE I

| Molar Conc. | Relaxivities, msec. | | | |
|---|---|---|---|---|
| | $T_1$ (Water) | $T_2$ (Water) | $T_1$ (Plasma) | $T_2$ (Plasma) |
| 0.010 | 43 | 41 | 40 | 34 |
| 0.005 | 100 | 86 | 74 | 68 |
| 0.0025 | 175 | | 139 | 124 |
| 0.00125 | 332 | | 240 | |
| 0.000625 | 639 | | 398 | |
| 0.000312 | 1083 | | 624 | |
| 0.000156 | 1470 | | 856 | |
| 0.000078 | | | 995 | |
| 0.000039 | | | 1103 | |

EXAMPLE 9

Organ Distribution of Mn(DPDP) in Rabbits

Each of four rabbits was injected intravenously with one of the following amounts of the solution obtained in Example 7: 0.01 mmoles/kg, 0.05 mmoles/kg, 0.10 mmoles/kg and 0.20 mmoles/kg. The rabbits were sacrificed 30 min post injection, and the proton relaxation values of selected body organs were measured with NMR, in vitro at 10 MHz. The relaxation rates found are shown in Table II.

TABLE II

| | Normal Values | | Relaxivities, msec. Observed Values | | | | | | | |
|---|---|---|---|---|---|---|---|---|---|---|
| | Dose (mmol/kg) | | 0.01 | | 0.05 | | 0.10 | | 0.20 | |
| Tissue | $T_1$ | $T_2$ | $T_1$ | $T_2$ | $T_1$ | $T_2$ | $T_1$ | $T_2$ | $T_1$ | $T_2$ |
| Brain | — | — | 554 | 76 | 496 | 82 | 590 | 90 | 352 | 66 |
| Heart | 605 | 70 | — | — | 353 | 54 | 300 | 51 | 205 | 47 |
| Lung | 595 | 112 | — | — | 575 | 113 | 435 | 61 | 376 | 63 |
| Fat | 171 | 154 | — | — | 200 | 139 | 183 | 115 | 192 | — |
| Skel. Musc. | 423 | 47 | — | — | 494 | 47 | 425 | 31 | 232 | 31 |
| Renal Cort. | 338 | 85 | 298 | 65 | 210 | 57 | 188 | 55 | 143 | 53 |
| Renal Med. | 672 | 149 | 502 | 99 | 223 | 57 | 209 | 48 | 127 | 60 |
| Liver | 252 | 64 | 176 | 39 | 76 | 31 | 65 | 23 | 68 | 25 |
| Stom. | 349 | 69 | — | — | 245 | 41 | 242 | 52 | 271 | 53 |
| Small Int. | 352 | 79 | 324 | 72 | 237 | 52 | 218 | 46 | 131 | 46 |
| Large Int. | 349 | 77 | 283 | 64 | 365 | 83 | 290 | 57 | 256 | 74 |
| Urine | — | — | 821 | — | 150 | 136 | 90 | 75 | — | — |
| Blood | 900 | — | 844 | — | 613 | — | 506 | — | 411 | — |

The organ distribution data is plotted in FIG. 2, with the following symbols:

| Liver -l- | Heart -h- | Cortex -c- |
|---|---|---|
| Medula -m- | Urine -u- | Blood -b- |

It shows rapid uptake of the Mn(DPDP) in the heart, liver and kidneys. The liver and kidneys are saturated with a dose of 0.10 mmole/kg while the heart continues to uptake Mn(DPDP) through the dose range studied. The complex of Mn(DPDP) may cross the intake-brain barrier as uptake by the brain was observed at higher doses. In cases where a defect is present in the blood-brain barrier (through disease or trauma), large amounts of the complex of Mn(DPDP) collect in the extravascular space and such defects were observed by NMRI tomography. The same defects are not observable without the use of Mn(DPDP) as a contrast agent.

EXAMPLE 10

Pharmacokinetics with Mn(DPDP)

Each of seven rabbits was injected intravenously with 0.01 mmol/kg of the solution obtained in Example 7. The rabbits were sacrificed at 0.25, 0.50, 1.0, 2.0, 4, 6 and 24 hours post-injection, and the proton relation values of selected body organs were measured with NMR, in vitro, at 10 MHz. The $T_1$ relaxation rates are shown in Table III.

TABLE III

| | $T_1$ Relaxivities, msec | | | | | | | $T_1$ Normal |
|---|---|---|---|---|---|---|---|---|
| | Time, hr | | | | | | | |
| Tissue | 0.25 | 0.50 | 1.0 | 2 | 4 | 6 | 24 | Value |
| Liver | 68 | 76 | 48 | 48 | 145 | 209 | 315 | 250 ± 50 |
| Bile | 160 | 46 | 25 | 21 | <1 | 14 | 107 | 275 ± 55 |
| Renal cortex | 202 | 191 | 229 | 192 | 210 | 239 | 328 | 338 ± 60 |
| Renal medulla | 192 | 231 | 236 | 310 | 340 | 375 | 563 | 672 ± 100 |
| Heart | 231 | 352 | 381 | 507 | 522 | 663 | 660 | 605 ± 100 |

The pharmacokinetic data show rapid uptake and clearance of Mn(DPDP) in the liver, renal cortex, renal medulla and heart. The results indicate clearance of Mn(DPDP) through both the renal and hepatobiliary systems within 6-8 hours post-injection.

EXAMPLE 11

Potentiometric Titrations

The compound DPDP was studied potentiometrically from pH 11.2 to 2.0. Data sets were collected on a custom-built automatic potentiometric titration apparatus composed of a METROHM 655 DOSIMAT automatic buret, a FISHER ACCUMET pH meter with a CORNING calomel combination electrode, a custom-blown water jacketed titration cell, a BRINKMAN LAUDA K-2/R constant temperature bath and a COMMODORE 64 computer. The BASIC computer program TITRATOR (Harris, W. et al, *J.Am.Chem.-Soc.* 101:6534 (1979)) runs the apparatus. Data analysis was performed on an IBM-AT computer using the least squares program, BETA (Harris, W. et al, supra), and the data analysis program, HANDNBAR (Harris, W. et al, supra). The titrants were standardized by phenophthalein titration as follows: KOH was calibrated against potassium hydrogen phthalate (a primary standard), and HCl solutions were calibrated against the KOH standard. The Mn(II)Cl$_2$ solution was standardized with an EDTA titration using Erichrome Black T as the indicator. All solutions were made from distilled, deionized water that was further purified on a MILLI-Q cartridge system, degassed, and then kept under an atmosphere of argon which had been scrubbed for $CO_2$ and $O_2$. Additions of EDTA and Mn(II) solutions were performed using calibrated GILMOT pipets. The electrode was calibrated in concentration units with degassed solutions of p[H+]=2.291 and 1.078 at 0.1M ionic strength.

The ligand proton titration was performed by adding 28.7 mg (0.045 mmoles) to 54.6 ml of a high pH aqueous solution. It was then titrated to low pH with 0.1009N HCl.

The metal complex titration was performed by adding 152.2 mg (0.2383 mmoles) to 74.6 ml of a high pH aqueous solution. 2.07 ml of a 0.1152M Mn(II) solution (0.2386 mmoles) were added. The complex was then titrated to low pH with 1.002N HCl.

The data obtained was analyzed using a model that consisted of eight one-proton steps. The first two protonation equilibria were outside of the range of the titration window afforded by the concentration of titrant and were therefore estimated based on work by Martell and co-workers reported by Taliaferro, C. et al, *Inorg.Chem.* 24:2408-2413 (1985). Refinement of the remaining equilibria yielded constants with calculated e.s.d.'s (log K) of less than 0.02. Assignment of the protonation sites (pK's) was based on work by Martell and co-workers (Taliaferro, et al, supra), and is shown in FIG. 1.

At a pH of 3 and above, the ligand is anionic and possesses deprotonated metal binding sites, both important criteria for a metal chelating agent.

EXAMPLE 12

N,N'-bis-(pyridoxal-5-phosphate)alkylenediamine-N,N'-diacetic acids

Repeating the procedure of Examples 5 and 6 but replacing the diamine of Example 3 with the products of Example 4 yields N,N'-bis(pyridoxal-5-phosphate)-1,3-(n-propylene)-N,N'-diacetic acid, N,N'-bis(pyridoxal-5-phosphate)-1,2-(n-propylene)-N,N'-diacetic acid, N,N'-bis(pyridoxal-5-phosphate)-1,2-isopropylene-N,N'-diacetic acid, N,N'-bis(pyridoxal-5-phosphate)-1,2-(n-butylene)-N,N'-diacetic acid, N,N'-bis(pyridoxal-5-phosphate)-1,4-(n-butylene)-N,N'-diacetic acid, N,N'-bis(pyridoxal-5-phosphate)-1,3-(n-butylene)-N,N'-diacetic acid, and N,N'-bis(pyridoxal-5-phosphate)-1,2-(3-methylene)propyl-N,N'-diacetic acid.

EXAMPLE 13

DPDP Chelates

Repeating the procedure of Example 7 but replacing manganese dichloride tetrahydrate with equimolar amounts of the soluble chlorides of $Cr^{+3}$, $Fe^{+2}$, $Fe^{+3}$, $Co^{+3}$, $Ni^{+2}$, $Cu^{+2}$, $Pr^{+3}$, $Nd^{+3}$, $Sm^{+3}$, $Yb^{+3}$, $Gd^{+3}$, $Tb^{+3}$, $Dy^{+3}$, $Ho^{+3}$, or $Er^{+3}$ yields the corresponding sodium salts of the respective metal ion chelates of N,N'-bis-(pyridoxal-5-phosphate)ethylenediamine-N,N'-diacetic acid. The procedure can be repeated replacing the metal chloride salts with soluble nitrate or sulfate salts.

EXAMPLE 14

Other Chelates

Repeating the procedure of Example 7 but replacing N,N'-bis-(pyridoxal-5-phosphate)ethylenediamine-N,N'-diacetic acid with equimolar amounts of the chelate forming compounds produced in accordance with Example 10, and replacing manganese dichloride tetrahydrate with equimolar amounts of the soluble chlorides, carbonates or nitrates of $Cr^{+3}$, $Fe^{+2}$, $Fe^{+3}$, $Co^{+3}$, $Ni^{+2}$, $Cu^{+2}$, $Pr^{+3}$, $Nd^{+3}$, $Sm^{+3}$, $Yb^{+3}$, $Gd^{+3}$, $Tb^{+3}$, $Dy^{+3}$, $Ho^{+3}$, or $Er^{+3}$ yields the sodium-calcium salts of the respective metal ion chelates of N,N'-bis(pyridoxal-5-phosphate)-1,3-(n-propylene)-N,N'-diacetic acid,
N,N'-bis(pyridoxal-5-phosphate)-1,2-(n-propylene)-N,N'-diacetic acid,
N,N'-bis(pyridoxal-5-phosphate)-1,2-isopropylene-N,N'-diacetic acid,
N,N'-bis(pyridoxal-5-phosphate)-1,2-(n-butylene)-N,N'-diacetic acid,
N,N'-bis(pyridoxal-5-phosphate)-1,4-(n-butylene)-N,N'-diacetic acid,
N,N'-bis(pyridoxal-5-phosphate)-1,3-(n-butylene)-N,N'-diacetic acid, and
N,N'-bis(pyridoxal-5-phosphate)-1,2-(3-methylene)propyl-N,N'-diacetic acid.

EXAMPLE 15

N,N'-bis(pyridoxal-5-phosphate)-trans-1,2-cyclohexylenediimine

A 26.5 gm quantity (0.1 mole) of pyridoxal-5-phosphate was dissolved in 300 ml of methanol, and 38 ml of 5N NaOH was added. Then 5.71 gm (0.05 mole) of trans-1,2-diaminocyclohexane was added with stirring, and the volume of the solution was reduced to 200 ml in vacuo. After cooling to 0° C., the yellow imine was isolated by filtration, washed with diethyl ether, and dried in vacuo to yield 17 gm of sodium N,N'-bis(pyridoxal-5-phosphate)-trans-1,2-cyclohexylenediimine or sodium 5-(N-(3-hydroxy-2-methyl-5-phosphonomethyl-4-pyridyl)methylideneamino-trans-1,2-cyclohexyleneiminome thyl)-2-hydroxy-3-methyl-5-pyridylmethylphosphate (49% yield, melting point 200° C.-205° C. with decomposition).

EXAMPLE 16

Other N,N'-bis(pyridoxal-5-phosphate)-1,2-cyclo(alkylene or arylene)diimines Repeating the procedure of Example 15 but replacing the trans-1,2-diaminocyclohexane with trans-1,2-diaminocyclopentane, trans-1,2-diaminocycloheptane, trans-1,2-diaminocyclooctane, cis-1,2-diaminocyclohexane, trans-1,3-diaminocyclohexane, trans-1,4-diaminocyclohexane, o-aminoaniline and cis-1,4-diaminocyclohexane yields the corresponding N,N'-bis(pyridoxal-5-phosphate)-trans-1,2-cyclopentylenediimine,
N,N'-bis(pyridoxal-5-phosphate)-trans-1,2-cycloheptylenediimine,
N,N'-bis(pyridoxal-5-phosphate)-trans-1,2-cyclooctylenediimine,
N,N'-bis(pyridoxal-5-phosphate)-cis-1,2-cyclohexylenediimine,
N,N'-bis(pyridoxal-5-phosphate)-trans-1,3-cyclohexylenediimine,
N,N'-bis(pyridoxal-5-phosphate)-trans-1,4-cyclohexylenediimine,
N,N'-bis(pyridoxal-5-phosphate)-1,2-phenylenediimine, and
N,N'-bis(pyridoxal-5-phosphate)-cis-1,4-cyclohexylenediimine.

EXAMPLE 17

N,N'-bis(pyridoxal-5-phosphate)-trans-1,2-cyclohexylenediamine

A 14 gm (0.02 mole) portion of the diimine product of Example 15 was dissolved in 200 ml of 1:1 water: methanol. The resulting solution was sparged with argon, and 1.0 gm of 5% platinum on carbon was added. The system was flushed with hydrogen. The hydrogen pressure was increased to 50 psig for 16 hr at 25° C. The reaction product was filtered through CELITE, and the resulting solution of N,N'-bis(pyridoxal-5-phosphate)-trans-1,2-cyclohexyldiamine or sodium 5-(N-(3-hydroxy-2-methyl-5-phosphonomethyl-4-pyridyl)methylideneamino-trans-1,2-cyclohexyliminomethyl)-2-hydroxy-3-methyl-5-pyridylmethylphosphate was concentrated in vacuo to about 20 ml and cooled to 0° C. to induce crystallization. The product was isolated by filtration, washed with cold $H_2O$ and dried in vacuo. $^1H$ NMR ($D_2O$, 400 MHz) delta 7.45 (s, pyr-$\underline{H}$), 4.53 (d, $CH_2OP$, $J_{HP}$=4.9 Hz), 3.83 (dd, N—$CH_2$-pyr), 2.72 (br s, cyclo-$(CH_2)_4(CH)_2(NH)_2$—), 1.88 (s, pyr-$CH_3$), 1.83-1.08 (3 br s, cyclo-$(CH_2)_4(CH)_2(NH)_2$—).

EXAMPLE 18

N,N'-bis(pyridoxal-5-phosphate)-1,2-cyclo(alkylene or arylene)diamines

Repeating the procedure of Example 17 but replacing the diimine product of Example 15 with the diimine products prepared in accordance with the procedure of Example 16 yields the corresponding diamines:

N,N'-bis(pyridoxal-5-phosphate)-trans-1,2-cyclopentylenediamine,
N,N'-bis(pyridoxal-5-phosphate)-trans-1,2-cycloheptylenediamine,
N,N'-bis(pyridoxal-5-phosphate)-trans-1,2-cyclooctylenediamine,
N,N'-bis(pyridoxal-5-phosphate)-cis-1,2-cyclohexylenediamine,
N,N'-bis(pyridoxal-5-phosphate)-trans-1,3-cyclohexylenediamine,
N,N'-bis(pyridoxal-5-phosphate)-trans-1,4-cyclohexylenediamine.
N,N'-bis(pyridoxal-5-phosphate)-1,2-phenylenediamine, and
N,N'-bis(pyridoxal-5-phosphate)-cis-1,4-cyclohexylenediamine.

EXAMPLE 19

N,N'-bis-(pyridoxal-5-phosphate)-trans-1,2-cyclohexylenediamine-N,N'-diacetic acid The diamine from Example 17 was charged to a one liter 3-neck flask, and the pH was adjusted to 11 with 5N NaOH. Then 5.6 gm (0.04 mole) of bromoacetic acid was dissolved in 10 ml of water and added dropwise to the stirred diamine solution while maintaining the pH at 11. The reaction was warmed to 50° C. and stirred for 16 hr. 50 gm of weakly acidic cation exchange resin (AMBERLITE IRC-50) was added, and the pH dropped to 6.7. The resin was removed by filtration, and 15 gm of cation exchange resin (DOWEX 50W-X8) was added. The pH dropped to 3.8.

The solution was filtered, and all of the solvent was evaporated from the filtrate to yield a foamy solid. The solid was dissolved in 30 ml of 88% formic acid, and the product was precipitated by the addition of 150 ml of methanol followed by 150 ml of ethanol. The solvent mixture was decanted from the gummy solid and discarded. The solid was dissolved in a minimum amount of deionized water (about 100 ml), and the product was allowed to stand overnight at 25° C. The product was isolated by filtration, washed with 50 ml of cold water, 25 ml of ethanol and then dried in vacuo to yield the product. The compound was recrystallized by the same procedure to yield N,N'-bis-(pyridoxal-5-phosphate)-trans-1,2-cyclohexylenediamine-N,N'-diacetic acid or N,N'-bis(3-hydroxy-2-methyl-5-phosphonomethyl-4-pyridylmethyl)-trans-1,2-cyclohexylenediamine-N,N'-diacetic acid (DPCP) with a melting point (decomposition) of 221° C.–226° C. $^1$H NMR (D$_2$O, 400 MHz) delta 7.53 (s, pyr-$\underline{H}$), 4.58 (d, CH$_2$OP, J$_{HP}$=5.9 Hz), 3.89 (dd, N—C$\underline{H}_2$-pyr, 3.31 (s, C$\underline{H}_2$COOH), 2.78 (br s, cyclo-(CH$_2$)$_4$(C$\underline{H}$)$_2$(NH)$_2$—), 1.93 (s, pyr-C$\underline{H}_3$), 1.90–1.15 (3 br s, cyclo-(C$\underline{H}_2$)$_4$(CH)$_2$(NH)$_2$—).

EXAMPLE 20

N,N'-bis-(pyridoxal-5-phosphate)-cyclo(alkylene and arylene)diamine-N,N'-diacetic acids Repeating the procedure of Example 19 but replacing the diamine of Example 17 with the diamines of Example 18 yields the corresponding:

N,N'-bis(pyridoxal-5-phosphate)-trans-1,2-cyclopentylenediamine-N,N'-diacetic acid,
N,N'-bis(pyridoxal-5-phosphate)-trans-1,2-cycloheptylenediamine-N,N'-diacetic acid,
N,N'-bis(pyridoxal-5-phosphate)-trans-1,2-cyclooctylenediamine-N,N'-diacetic acid,
N,N'-bis(pyridoxal-5-phosphate)-cis-1,2-cyclohexylenediamine-N,N'-diacetic acid,
N,N'-bis(pyridoxal-5-phosphate)-trans-1,3-cyclohexylenediamine-N,N'-diacetic acid,
N,N'-bis(pyridoxal-5-phosphate)-trans-1,4-cyclohexylenediamine-N,N'-diacetic acid,
N,N'-bis(pyridoxal-5-phosphate)-1,2-phenylenediamine-N,N'-diacetic acid, and
N,N'-bis(pyridoxal-5-phosphate)-cis-1,4-cyclohexylenediamine-N,N'-diacetic acid.

EXAMPLE 21

Chelates

Repeating the procedure of Example 7 but replacing N,N'-bis-(pyridoxal-5-phosphate)ethylenediamine-N,N'-diacetic acid with equimolar amounts of the products of chelate forming compounds produced in accordance with Examples 19 and 20 and using equimolar amounts of the soluble chlorides, carbonates or nitrates of Mn$^{+2}$, Cr$^{+3}$, Fe$^{+2}$, Fe$^{+3}$, Co$^{+3}$, Ni$^{+2}$, Cu$^{+2}$, Pr$^{+3}$, Nd$^{+3}$, Sm$^{+3}$, Yb$^{+3}$, Gd$^{+3}$, Tb$^{+3}$, Dy$^{+3}$, Ho$^{+3}$, or Er$^{+3}$ yields the sodium-calcium salts of the respective metal ion chelates of N,N'-bis(pyridoxal-5-phosphate)-trans-1,2-cyclohexylenediamine-N,N'-diacetic acid,
N,N'-bis(pyridoxal-5-phosphate)-trans-1,2-cyclopentylenediamine-N,N'-diacetic acid,
N,N'-bis(pyridoxal-5-phosphate)-trans-1,2-cycloheptylenediamine-N,N'-diacetic acid,
N,N'-bis(pyridoxal-5-phosphate)-trans-1,2-cyclooctylenediamine-N,N'-diacetic acid,
N,N'-bis(pyridoxal-5-phosphate)-cis-1,2-cyclohexylenediamine-N,N'-diacetic acid,
N,N''-bis(pyridoxal-5-phosphate)trans-1,3-cyclohexylenediamine-N,N'-diacetic acid,
N,N'-bis(pyridoxal-5-phosphate)-trans-1,4-cyclohexylenediamine-N,N'-diacetic acid,
N,N'-bis(pyridoxal-5-phosphate)-1,2-phenylenediamine-N,N'-diacetic acid, and
N,N'-bis(pyridoxal-5-phosphate)-cis-1,4-cyclohexylenediamine-N,N'-diacetic acid.

EXAMPLE 22

Pyridoxal-5-phosphate (N-methylethanolamine)monoester 2.04 gm (0.01 mole) of pyridoxal hydrochloride is dissolved in 50 ml of dry THF containing 0.05 gm (0.02 mole) of sodium hydride with stirring. When gas evolution had ceased (about 15 min), 1.71 gm (0.01 mole) of benzyl bromide is added, and after stirring overnight, the solution is brought to dryness in vacuo. The sticky solid is suspended in 50 ml of dry methylene chloride and following addition of 3.0 gm (0.03 mole) of triethylamine, the slurry is cooled to 0° C. 1.38 gm (0.01 mole) of 2-chloro-3-methyl-1-oxa-3-aza-2-phosphacyclopentane (prepared by the method of Jones, et al, *J. Chem.-Soc. Perkin trans I.* p 199 (1985)) is added with vigorous stirring. The suspension is stirred for 1 hr at rm temp, and then 100 ml of water is added. The methylene chloride layer is separated, dried over MgSO$_4$, and the solvent removed in vacuo. Addition of diethyl ether yields the intermediate product as a hydroscopic white solid (1.8 gm, 50% yield). The intermediate is oxidized with excess dinitrogen tetroxide in methylene chloride at −78° C., and then is treated with aqueous HCl in THF under reflux to give the (N-methylethanolamine)monoester of pyridoxal-5-phosphate in an overall yield of 40%.

EXAMPLE 23

N,N'-bis(pyridoxal-5-phosphate(N-methylethanolamine)monoester)ethylenediimine

Repeating the procedure of Example 1 but replacing pyridoxal-5-phosphate with the product of Example 22 yields N,N'-bis(pyridoxal-5-phosphate(N-methylethanolamine)monoester)ethylenediimine or sodium 5-(N-(3-hydroxy-2-methyl-5-phosponomethyl-4-pyridyl)-methylideneaminoethyleneiminomethyl)-2-hydroxy-3-methyl-5-pyridylmethylphosphoric acid, N-methylethanolamine ester.

EXAMPLE 24

Other Monoester Diimines

Repeating the procedure of Example 23 with 1,3-diamino-n-propane, 1,2-diamino-n-propane, 1,2-diaminoisopropane, 1,2-diamino-n-butane, 1,4-diamino-n-butane, and 1,3-diamino-n-butane, 1,2-diamino-3-methylpropane yields the corresponding N,N'-bis(pyridoxal-5-phosphate(N-methyle-thanolamine)monoester)-1,3-(n-propylene)diimine,
N,N'-bis(pyridoxal-5-phosphate(N-methyle-thanolamine)monoester)-1,2-(n-propylene)diimine,
N,N'-bis(pyridoxal-5-phosphate(N-methyle-thanolamine)monoester)-1,2-isopropylenediimine,
N,N'-bis(pyridoxal-5-phosphate(N-methyle-thanolamine)monoester)-1,2-(n-butylene)diimine,
N,N'-bis(pyridoxal-5-phosphate(N-methyle-thanolamine)monoester)-1,4-(n-butylene)diimine,
N,N'-bis(pyridoxal-5-phosphate(N-methyle-thanolamine)monoester)-1,3-(n-butylene)diimine, and
N,N'-bis(pyridoxal-5-phosphate(N-methyle-thanolamine)monoester)-1,2-(3-methyl)propylenediimine.

Repeating the procedure of Example 23 with trans-1,2-diaminocyclohexane, trans-1,2-diaminocyclopentane, trans-1,2-diaminocycloheptane, trans-1,2-diaminocyclooctane, o-aminoaniline, and cis-1,2-diaminocyclohexane, yields the corresponding N,N'-bis(pyridoxal-5-phosphate(N-methyle-thanolamine)monoester)-trans-1,2-cyclohexylenediimine,
N,N'-bis(pyridoxal-5-phosphate(N-methyle-thanolamine)monoester)-trans-1,2-cyclopentylenediimine,
N,N'-bis(pyridoxal-5-phosphate(N-methyle-thanolamine)monoester)-trans-1,2-cycloheptylenediimine,
N,N'-bis(pyridoxal-5-phosphate(N-methyle-thanolamine)monoester)-trans-1,2-cyclooctylenediimine,
N,N'-bis(pyridoxal-5-phosphate(N-methyle-thanolamine)monoester)-1,2-phenylenediimine, and
N,N'-bis(pyridoxal-5-phosphate(N-methyle-thanolamine)monoester)-cis-1,2-cyclohexylenediimine.

EXAMPLE 25

N,N'-bis(pyridoxal-5-phosphate(N-methyle-thanolamine)monoester)ethylenediamine

Repeating the procedure of Example 3 but substituting the diimine product of Example 23 for the diimine product of Example 1 yields N,N'-bis(pyridoxal-5-phosphate(N-methyl-ethanolamine)monoester)ethylenediamine or 5-(N-(3-hydroxy-2-methyl-5-phosponomethyl-4-pyridyl)methylaminoethyleneaminomethyl)-2-hydroxy-3-methyl-5-pyridylmethylphosphoric acid, N-methyl-ethanolamine ester.

EXAMPLE 26

Other Monoester Diamines

Repeating the procedure of Example 25 but substituting the diimine products of Example 24 for the diimine product of Example 23 yields
p0     N,N'-bis(pyridoxal-5-phosphate(N-methyle-thanolamine)monoester)-1,3-(n-propylene)diamine,
N,N'-bis(pyridoxal-5-phosphate(N-methyle-thanolamine)monoester)-1,2-(n-propylene)diamine,
N,N'-bis(pyridoxal-5-phosphate(N-methyle-thanolamine)monoester)-1,2-isopropylenediamine,
N,N'-bis(pyridoxal-5-phosphate(N-methyle-thanolamine)monoester)-1,2-(n-butylene)diamine,
N,N'-bis(pyridoxal-5-phosphate(N-methyle-thanolamine)monoester)-1,4-(n-butylene)diamine,
N,N'-bis(pyridoxal-5-phosphate(N-methyle-thanolamine)monoester)-1,3-(n-butylene)diamine,
N,N'-bis(pyridoxal-5-phosphate(N-methyle-thanolamine)monoester)-1,2-(3-methyl)propylenediamine,
N,N'-bis(pyridoxal-5-phosphate(N-methyle-thanolamine)monoester)-trans-1,2-cyclohexylenediamine,
N,N'-bis(pyridoxal-5-phosphate(N-methyle-thanolamine)monoester)-trans-1,2-cyclopentylenediamine,
N,N'-bis(pyridoxal-5-phosphate(N-methyle-thanolamine)monoester)-trans-1,2-cycloheptylenediamine,
N,N'-bis(pyridoxal-5-phosphate(N-methyle-thanolamine)monoester)-trans-1,2-cyclooctylenediamine,
N,N'-bis(pyridoxal-5-phosphate(N-methyle-thanolamine)monoester)-1,2-phenylenediamine, and
N,N'-bis(pyridoxal-5-phosphate(N-methyle-thanolamine)monoester)-cis-1,2-cyclohexylenediamine.

EXAMPLE 27

DPDP-phosphate monoester

Repeating the procedure of Examples 5 and 6 but replacing the diamine of Example 3 with the product of Example 25 yields N,N'-bis(pyridoxal-5-phosphate-(N-methyl-ethanolamine)monoester)ethylenediamine-N,N'-diacetic acid, sodium salt or N-methylethanolamine phosphate ester of 5-(N-(3-hydroxy-2-methyl-5-phosponomethyl-4-pyridyl)methylaminoethyleneaminomethyl)-2-hy droxy-3-methyl-5-pyridylmethylphosphoric acid, sodium salt.

EXAMPLE 28

Other Diamine-N,N'-diacetic Acid Phosphate Monoesters

Repeating the procedure of Example 27 but replacing the products of Example 26 for the product of Example 25 yields N,N'-bis(pyridoxal-5-phosphate(N-methyle-thanolamine)monoester)-1,3-(n-propylene)diamine-N,N'-diacetic acid salt,
N,N'-bis(pyridoxal-5-phosphate(N-methyle-thanolamine)monoester)-1,2-(n-propylene)diamine-N,N'-diacetic acid salt,
N,N'-bis(pyridoxal-5-phosphate(N-methyle-thanolamine)monoester)-1,2-isopropylenediamine-N,N'-diacetic acid salt,
N,N'-bis(pyridoxal-5-phosphate(N-methyle-thanolamine)monoester)-1,2-(n-butylene)diamine-N,N'-diacetic acid salt,
N,N'-bis(pyridoxal-5-phosphate(N-methyle-thanolamine)monoester)-1,4-(n-butylene)diamine-N,N'-diacetic acid salt,
N,N'-bis(pyridoxal-5-phosphate(N-methyle-thanolamine)monoester)-1,3-(n-butylene)diamine-N,N'-diacetic acid salt,
N,N'-bis(pyridoxal-5-phosphate(N-methyle-thanolamine)monoester)-1,2-(3-methyl)propylenediamine-N,N'-diacetic acid salt, N,N'-bis(pyridoxal-5-phosphate(N-methyle-
thanolamine)monoester)-trans-1,2-cyclohexylenedia-
mine-N,N'-diacetic acid salt,
N,N'-bis(pyridoxal-5-phosphate(N-methyle-
thanolamine)monoester)-trans-1,2-cyclopen-
tylenediamine-N,N'-diacetic acid salt,
N,N'-bis(pyridoxal-5-phosphate(N-methyle-
thanolamine)monoester)-trans-1,2-cyclohep-
tylenediamine-N,N'-diacetic acid salt,
N,N'-bis(pyridoxal-5-phosphate(N-methyle-
thanolamine)monoester)-trans-1,2-cyclooctylenedia-
mine-N,N'-diacetic acid salt,
N,N'-bis(pyridoxal-5-phosphate(N-methyle-
thanolamine)monoester)-1,2-phenylenediamine-
N,N'-diacetic acid salt, and
N,N'-bis(pyridoxal-5-phosphate(N-methyle-
thanolamine)monoester)-cis-1,2-cyclohexylenedia-
mine-N,N'-diacetic acid salt.

EXAMPLE 29

Chelates

Repeating the procedure of Example 7 but replacing N,N'-bis-(pyridoxal-5-phosphate)ethylenediamine-N,N'-diacetic acid with an equimolar amount of the chelate forming compound produced in accordance with Example 27, yields the sodium-calcium Mn(II) chelate of N,N'-bis(pyridoxal-5-phosphate-(N-methyl-ethanolamine)monoester)ethylenediamine-N,N'-diacetic acid.

Repeating this procedure, replacing manganese dichloride tetrahydrate with equimolar amounts of the soluble chlorides, carbonates or nitrates of $Cr^{+3}$, $Fe^{+2}$, $Fe^{+3}$, $Co^{+3}$, $Ni^{+2}$, $Cu^{+2}$, $Pr^{+3}$, $Nd^{+3}$, $Sm^{+3}$, $Yb^{+3}$, $Gd^{+3}$, $Tb^{+3}$, $Dy^{+3}$, $Ho^{+3}$, or $Er^{+3}$ yields the sodium-calcium salts of the respective metal ion chelates of N,N'-bis(pyridoxal-5-phosphate-(N-methyl-ethanolamine)monoester)ethylenediamine-N,N'-diacetic acid.

EXAMPLE 30

Other Chelates

Repeating the procedures of Example 29 but replacing the products of Example 28 for the product of Example 27 yields the $Mn^{+2}$, $Cr^{+3}$, $Fe^{+2}$, $Fe^{+3}$, $Co^{+3}$, $Ni^{+2}$, $Cu^{+2}$, $Pr^{+3}$, $Nd^{+3}$, $Sm^{+3}$, $Yb^{+3}$, $Gd^{+3}$, $Tb^{+3}$, $Dy^{+3}$, $Ho^{+3}$, or $Er^{+3}$ ion chelates of the sodium-calcium salts of the diacetic acid chelating agents of Example 28.

EXAMPLE 31

DPDP-(mono)acetic Acid Analog Synthesis 10 gms (0.017 mole) of the diamine from Example 3 was dissolved in 25 ml of 1:1 water/methanol and charged to a 250 ml 4-neck flask equipped with two addition funnels, pH electrode, thermometer and stir bar. 1.4 gms (0.035 mole) of NaOH and 2.4 gm (0.017 mole) of bromoacetic acid were each dissolved in 10 ml of deionized water and charged to the two addition funnels. Sufficient NaOH was added to the stirring diamine solution to bring the pH to about 11, which raised the temperature to about 40° C. The temperature was maintained at 40° C., and bromoacetic acid and NaOH were added concurrently to maintain the pH at 11 over the course of 3 hr. The reaction was monitored by HPLC. Dowex 50W-X8 resin was added to lower the pH from 11.1 to 3.1, the solution was filtered, and resin was washed with 100 ml of deionized water. The pH of the filtrate was about 3.3. 5 ml of 97% formic acid was added, and the pH dropped to 3.0. Then 10 ml of isopropyl alcohol was added with a few seed crystals, the product stirred overnight at 30° C. to 40° C., and then allowed to cool to 25° C. The crude product was collected by filtration and washed with deionized water. The crude product was then dried at 50° C. in vacuo to yield 3 gms of product (30% yield). The product can be recrystallized from a formic acid/water mixture to yield 2.4 gms in 96-98% purity by HPLC to yield N,N'-bis-(pyridoxal-5-phosphate)ethylenediamine-N-acetic acid.

EXAMPLE 32

Other (Mono)acetic Acids

Repeating the procedure of Example 31 with the products of Examples 4, 17 and 18 yields the corresponding N,N'-bis(pyridoxal-5-phosphate)-1,3-(n-propylene)dia-
mine-N-acetic acid,
N,N'-bis(pyridoxal-5-phosphate)-1,2-(n-propylene)dia-
mine-N-acetic acid,
N,N'-bis(pyridoxal-5-phosphate)-1,2-isopropylenedia-
mine-N-acetic acid,
N,N'-bis(pyridoxal-5-phosphate)-1,2-(n-butylene)dia-
mine-N-acetic acid,
N,N'-bis(pyridoxal-5-phosphate)-1,4-(n-butylene)dia-
mine-N-acetic acid,
N,N'-bis(pyridoxal-5-phosphate)-1,3-(n-butylene)dia-
mine-N-acetic acid,
N,N'-bis(pyridoxal-5-phosphate)-1,2-(3-methyl)-
propylenediamine-N-acetic acid,
N,N'-bis(pyridoxal-5-phosphate)-trans-1,2-cyclohex-
ylenediamine-N-acetic acid,
N,N'-bis(pyridoxal-5-phosphate)-trans-1,2-cyclopen-
tylenediamine-N-acetic acid,
N,N'-bis(pyridoxal-5-phosphate)-trans-1,2-cyclohep-
tylenediamine-N-acetic acid,
N,N'-bis(pyridoxal-5-phosphate)-trans-1,2-cyclooc-
tylenediamine-N-acetic acid,
N,N'-bis(pyridoxal-5-phosphate)-cis-1,2-cyclohex-
ylenediamine-N-acetic acid,
N,N'-bis(pyridoxal-5-phosphate)-trans-1,3-cyclohex-
ylenediamine-N-acetic acid,
N,N'-bis(pyridoxal-5-phosphate)-trans-1,4-cyclohex-
ylenediamine-N-acetic acid,
N,N'-bis(pyridoxal-5-phosphate)-1,2-phenylenedia-
mine-N-acetic acid, and
N,N'-bis(pyridoxal-5-phosphate)-cis-1,4,2-cyclohex-
ylenediamine-N-acetic acid.

EXAMPLE 33

Other Chelates

Repeating the procedures of Example 29 but replacing the products of Example 32 for the product of Example 27 yields the $Mn^{+2}$, $Cr^{+3}$, $Fe^{+2}$, $Fe^{+3}$, $Co^{+3}$, $Ni^{+2}$, $Cu^{+2}$, $Pr^{+3}$, $Nd^{+3}$, $Sm^{+3}$, $Yb^{+3}$, $Gd^{+3}$, $Tb^{+3}$, $Dy^{+3}$, $Ho^{+3}$, or $Er^{+3}$ ion chelates of the sodium-calcium salts of the monoacetic acid chelating agents of Example 32.

EXAMPLE 34

N-pyridoxal-N'-(pyridoxal-5-phosphate)ethylenediimine

A 25 gm (0.123 mole) quantity of pyridoxal hydrochloride is slurried in 100 ml of methanol, and 4.88 gm (0.123 mole) of NaOH is added. When the solution is homogeneous, it is added dropwise to 7.5 gm of 1,2-diaminoethane in 100 ml of methanol with stirring. After 60 min, a methanol solution containing 32.7 gm (0.123 mole) of pyridoxal-5-phosphate and 4.88 gm (0.123 mole) of NaOH is added with vigorous stirring. The unsymmetrical imine product, 5-(N-(3-hydroxy-5-hydroxymethyl-2-methyl-4-pyridyl)methylideneaminoethyleneiminomethyl)-2-hydroxy-3-methyl-5pyridylmethylphosphoric acid or N-pyridoxal-N'-(pyridoxal-5-phosphate)-ethylenediimine, is stirred for 1 hr, and the product is isolated by filtration. The diimine is washed with methanol (2×50 ml) and diethyl ether (2×50 ml), and dried in vacuo.

EXAMPLE 35

N-pyridoxal-N'-(pyridoxal-5-phosphate)ethylenediamine

Repeating the procedure of Example 3 but substituting the diimine product of Example 34 for the diimine product of Example 1 yields the corresponding diamine product, 5-(N-(3-hydroxy-5-hydroxymethyl-2-methyl-4-pyridyl)methylaminoethyleneaminomethyl)-2-hydroxy-3-me thyl-5-pyridylmethylphosphoric acid or
N-pyridoxal-N'-(pyridoxal-5-phosphate)-ethylenediamine.

EXAMPLE 36

DPMP Synthesis

Repeating the procedures of Example 5 and 6 with the product of Example 35 yields the corresponding N-pyridoxal-N'-(pyridoxal-5-phosphate)ethylenediamine-N,N'-diacetic acid or
N-(3-hydroxy-5-hydroxyomethyl-2-methyl-4-pyridylmethyl)N'-(3-hydroxy-2-methyl-5-phosphonomethyl-4-pyridylmethyl)ethylenediamine-N,N'-diacetic acid (DPMP).

EXAMPLE 37

Other Chelates

Repeating the procedures of Example 29 but replacing the product of Example 36 for the product of Example 27 yields the $Mn^{+2}$, $Cr^{+3}$, $Fe^{+2}$, $Fe^{+3}$, $Co^{+3}$, $Ni^{+2}$, $Cu^{+2}$, $Pr^{+3}$, $Nd^{+3}$, $Sm^{+3}$, $Yb^{+3}$, $Gd^{+3}$, $Tb^{+3}$, $Dy^{+3}$, $Ho^{+3}$, or $Er^{+3}$ ion chelates of the sodium-calcium salts of N-pyridoxal-N'-(pyridoxal-5-phosphate)ethylenediamine-N,N'-diacetic acid.

We claim:

1. An improvement in the method of performing NMR imaging with a patient, comprising administering to the patient an effective amount of a chelate of a compound of the formula I with a metal ion having an atomic number within the range of 21 to 29, 42, 44, or 58–70:

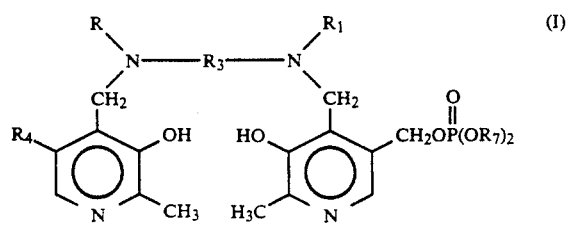

wherein

R is hydrogen or

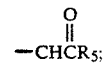

$R_1$ is hydrogen or

with the proviso that at least one of R and $R_1$ is other than hydrogen;

$R_5$ and $R_6$ are each, independently, hydroxy, alkoxy having from 1 to 18 carbons, hydroxy-substituted alkoxy having from 1 to 18 carbons, amino, or alkylamido having from 1 to 10 carbons;

$R_3$ is alkylene having from 1 to 8 carbons, 1,2-cycloalkylene having from 5 to 8 carbons, or 1,2-arylene having from 6 to 10 carbons;

$R_4$ is hydrogen, hydroxymethyl, alkyl having from 1 to 6 carbons, or

each $R_7$ is, independently, hydrogen, hydroxy-substituted alkyl having from 1 to 18 carbons; or a physiologically biocompatible inorganic or organic cation salt of said chelatable compound.

2. A method according to the formula I of claim 1 wherein each $R_7$ is, independently, hydrogen.

* * * * *